(12) United States Patent
Priestley et al.

(10) Patent No.: US 8,106,014 B2
(45) Date of Patent: Jan. 31, 2012

(54) METHODS AND APPARATUS FOR ENHANCED GROWTH OF PERIPHERAL NERVES AND NERVOUS TISSUE

(75) Inventors: John Priestley, London (GB); Von King, London (GB); David Philip Knight, New Greenham Business Park (GB); Nicholas James Vavasor Skaer, New Greenham Business Park (GB); Jessica Hensman, New Greenham Business Park (GB)

(73) Assignee: Neurotex Limited (GB)

( * ) Notice: Subject to any disclaimer, the term of this patent is extended or adjusted under 35 U.S.C. 154(b) by 738 days.

(21) Appl. No.: 11/575,268

(22) PCT Filed: Sep. 8, 2005

(86) PCT No.: PCT/GB2005/003456
§ 371 (c)(1),
(2), (4) Date: Nov. 9, 2008

(87) PCT Pub. No.: WO2006/030182
PCT Pub. Date: Mar. 23, 2006

(65) Prior Publication Data
US 2009/0099580 A1    Apr. 16, 2009

(30) Foreign Application Priority Data

Sep. 14, 2004   (GB) .................................. 0420411.1
Oct. 5, 2004    (GB) .................................. 0422019.0

(51) Int. Cl.
*A61F 2/02*    (2006.01)
*A61K 38/17*   (2006.01)

(52) U.S. Cl. .... 514/17.7; 424/423; 606/152; 623/23.71; 623/23.76

(58) Field of Classification Search .................. None
See application file for complete search history.

(56) References Cited

U.S. PATENT DOCUMENTS

| 4,963,146 | A |   | 10/1990 | Li |
| 5,019,087 | A |   | 5/1991 | Nichols |
| 5,026,381 | A |   | 6/1991 | Li |
| 5,656,605 | A | * | 8/1997 | Hansson et al. ............. 424/422 |

(Continued)

FOREIGN PATENT DOCUMENTS

GB    2386841 A    10/2003
(Continued)

OTHER PUBLICATIONS

Ducker et al, Experimental Improvements in the Use of Silastic Cuff for Peripheral Nerve Repair, 1968, Journal of Neurosurgery, vol. 28, issue 6, pp. 582-587.

(Continued)

*Primary Examiner* — Jeffrey E Russel
(74) *Attorney, Agent, or Firm* — Brooks Kushman P.C.

(57) ABSTRACT

A medical device comprises a tubular body having a lumen and a long axis; and a plurality of silk elements laid substantially parallel along the long axis of the lumen of the tubular body. A method of manufacturing the medical device comprises forming the tubular body and introducing the silk elements into the lumen of the tubular body so as to lie substantially parallel along the long axis of the lumen of the tubular body. The device can be used in a method for the regeneration of nerve cells comprising the implantation of a medical device at a site for regeneration of nerves.

41 Claims, 9 Drawing Sheets

U.S. PATENT DOCUMENTS

| | | | |
|---|---|---|---|
| 5,834,029 | A | 11/1998 | Bellamkonda et al. |
| 6,090,117 | A | 7/2000 | Shimizu |
| 6,589,257 | B1 | 7/2003 | Shimizu |
| 6,676,675 | B2 | 1/2004 | Mallapragada et al. |
| 6,716,225 | B2 | 4/2004 | Li et al. |
| 7,674,882 | B2 * | 3/2010 | Kaplan et al. ............... 530/353 |
| 2003/0100108 | A1 | 5/2003 | Altman et al. |

FOREIGN PATENT DOCUMENTS

| | | |
|---|---|---|
| JP | 02369878 A | 12/2002 |
| JP | 2004173772 A | 6/2004 |
| WO | 9822155 A1 | 5/1998 |

OTHER PUBLICATIONS

Midgley et al, Silicone Rubber Sheathing as an Adjunct to Neural Anastomosis, 1968, Surgical Forum, vol. 19, pp. 519-528.

Lundborg et al, In Vivo Regeneration of Cut Nerves Encased in Silicone Tubes: Growth across a Six-Millimeter Gap, Jul. 1982, Journal of Neuropathology and Experimental Neurology, vol. 41, No. 4, pp. 412-422.

Molander et al, Regeneration of Peripheral Nerve Through a Polyglactin Tube, Jan. 1982, Muscle & Nerve, vol. 5, Issue 1, pp. 54-58.

Uzman et al, Mouse Sciatic Nerve Regeneration Through Semipermeable Tubes: A Quantitative Model, 1983, Journal of Neuroscience Research, vol. 9, Issue 3, pp. 325-338.

Restrepo et al, Fascicular Nerve Graft Using an Empty Perineurial Tube: An Experimental Study in the Rabbit, 1983, Microsurgery, vol. 4, Issue 2, pp. 105-112.

Restrepo et al, Empty Perineurial Tube Graft Used to Repair a Digital Nerve: A First Case Report, 1985, Microsurgery, vol. 6, Issue 2, pp. 73-77.

Nyilas et al, Peripheral Nerve Repair With Bioresorbable Prosthesis, 1983, Transactions of the American Society of Internal Artificial Organs, vol. 29, pp. 307-313.

Rosen et al, Fascicular Tubulization: A Cellular Approach to Peripheral Nerve Repair, Nov. 1983, Annals of Plastic Surgery, vol. 11, Issue 5, pp. 397-411.

Huang et al, Hypoxia-Induced Apoptosis in Adult Rat Dorsal Root Ganglion Neurons In Vitro, Feb. 8, 2005, NeuroReport, vol. 16, No. 2, pp. 89-93.

Priestley, Biomaterials and Spinal Cord Repair, Presentation to the British Neuroscience Association, Brighton, Apr. 5, 2005.

Press Release, British Neuroscience Association, Apr. 5, 2005.

* cited by examiner

METHODS AND APPARATUS FOR ENHANCED GROWTH OF PERIPHERAL NERVES AND NERVOUS TISSUE

This invention relates to a device suitable for enhancing the healing of peripheral nerves and central nervous tissue, its method for construction and use.

Depending on the site, peripheral nerve injury caused by trauma or surgery can lead to the loss of sensation and movement. The rate and extent of recovery is slow, often incomplete and variable. The resulting loss of function can be very distressing to the patient, for example injury to the cavernosal nerve results in male impotence. Spinal transection has even more serious consequences and there is no method as yet of restoring nervous connection across the injured spinal cord. The consequences of spinal cord injury include paralysis and wasting of voluntary muscles and complete sensory loss in dermatomes supplied caudad to the transection. Loss of control of urinary and rectal sphincters results in double incontinence. Furthermore, transections within the upper neck vertebrae lead to paralysis of the diaphragm as it is innervated from phrenic nerve emerging from the third to fifth neck vertebrae. It also results in paralysis of the intercostals muscles (innervated by thoracic nerves). So a transection in the upper neck stops breathing movements with potentially fatal consequences. It is therefore necessary to ventilate patients with this type of injury for the rest of their lives. Further, degenerative diseases such as Parkinson's disease and multiple sclerosis cause degeneration of nerve tracks in the central nervous system and frequently lead to debilitating and highly distressing conditions such as motor impairment, sensory loss and reduction in arousal.

Some degree of recovery after peripheral nerve injury is usual and results from regrowth and reconnection of axons. However no reconnection is seen after spinal transection in human beings and little reconnection is thought to take place in the brain after serious injury to nerve tracts.

Accordingly various attempts have been made to encourage the repair of nerves and nerve tracts.

Three approaches have been used for the surgical treatment of injured peripheral nerves: direct resuturing of abutted ends; autograft replacement; and the use of various materials, natural or synthetic designed to guide nerve reconnection. The first approach is limited. It may be impossible to bring the cut ends of the nerve sufficiently close to suture them and even if it is possible, the resulting scar tissue resulting from injury and surgical manipulation can prevent axons from crossing the anastomotic region sometimes resulting in a tangled knot of nerve tissue known as a neuroma. Where the gap is too long an autograft is the best option at present, for example suturing a portion of the patient's sural nerve harvested from the uninjured site and sutured in to replace the injured region of a nerve. The disadvantages of this approach include loss of sensation resulting from removal of the donor tissue graft, increased pain, impracticality of removing a sufficiently long graft where there is a long injured section to be replaced, increased risk of infection at the graft removal site and an additional scar. Further the repair procedure is time consuming and requires a great deal of skill.

A variety of alternative nerve graft materials have been tried including empty perineurium in the hope of overcoming the disadvantages of a nerve autograft. Although there is a long history of attempts to devise cuffs, conduits, wrappers and tubes in an attempt to provide channels for axon growth, and prevent infiltration with fibroblasts and neuroma formation, at present none of these give satisfactory results.

The earliest attempts to provide a conduit for nerve healing used a tube of collagen derived from decalcified bone. This generally resulted in fibrous union with no return of function. A wide range of other tissues and materials were tried subsequently including vessels, fascia, fat, muscle, fibrin, parchment, gelatine, and various metals. Failure in these devices resulted from fibrosis induced by the tissue injury and the implanted materials. The non-resorbable materials used often necessitated a further surgical procedure for their removal.

Improvements have been suggested on these early generation materials for providing conduits for injured peripheral nerves. For example, the use of silastic cuffs for peripheral nerve repair was reported by Ducker et al. in Vol. 28, Journal of Neurosurgery, pp. 582-587 (1968). Silicone rubber sheathing for nerve repair was reported by Midgley et al. in Vol. 19, Surgical Forum, pp. 519-528 (1968) and by Lundborg, et al. in Vol. 41, Journal of Neuropathology and Experimental Neurology, pp. 412-422 (1982). The use of bioresorbable polyglactin mesh tubing was reported by Molander et al. in Vol. 5, Muscle & Nerve, pp. 54-58 (1982). The use of semipermeable acrylic copolymer tubes in nerve regeneration was disclosed by Uzman et al. in Vol. 9, Journal of Neuroscience Research, pp. 325-338 (1983). Empty perineurial tubes have also been used as channels for bridging nerve gaps as disclosed in "Fascicular Nerve Graft Using An Empty Perineurial Tube: An Experimental Study in the Rabbit" by Y. Restrepo, et al., (Microsurgery 4: 105-112, 1983) and in "Empty Perineurial Tube Graft Used to Repair A Digital Nerve: A First Case Report" by Y. Restrepo, et al., (Microsurgery 6: 73-77, 1985). Bioresorbable nerve guidance channels of polyesters and other polymers have been reported by Nyilas et al. in Vol. 29, Transactions Am. Soc. Artif. Internal Organs, pp. 307-313 (1983). The use of a polyglycolic acid as an artificial perineurium is disclosed by Joseph M. Rosen, et al., in Ann. Plast. Surg. 11, pp 397-411.

U.S. Pat. No. 6,716,225 teaches the use of a longitudinally-ridged hollow conduit made from a biocompatible and bioresorbable biopolymeric material. U.S. Pat. Nos. 5,026,381, 4,963,146 and U.S. Pat. No. 5,019,087 teach a multi-walled hollow conduit with micro-porous walls made from type I collagen. U.S. Pat. No. 6,676,675 discloses the use of a sheet or tube with longitudinal ridges or tubes containing poly (vinyl alcohol) aimed at stimulating nerve regeneration. U.S. Pat. No. 6,589,257 discloses the use of a resorbable tube made from either polyglycolic acid, polylactic acid, poly (glycolic-lactic) copolymer or related synthetic resorbable materials and coated with gelatin or collagen and containing longitudinally oriented cross-linked collagen fibres coated with laminin. U.S. Pat. No. 6,090,117 teaches the use of a similar tube in which the spaces between the collagen fibrils are filled with a matrix gel containing collagen, laminin, heparan sulfate proteoglycans, entactin and growth factor. U.S. Pat. No. 5,834,029 teaches a biocompatible semi-permeable conduit containing a matrix derivatized by any one of three laminin sequences known to be important in cell binding.

Three peripheral nerve regeneration conduits have so far received FDA approval for clinical trials: the Salubria Nerve Cuff; the Integra Neurosciences resorbable collagen tube and the Neurogen Neurotube. The ability of these devices to stimulate healing of peripheral nerves leaves considerable room for improvement. None of these devices or the above mentioned materials or approaches are entirely satisfactory for repairing peripheral nerves and none have so far proved of use for stimulating the regeneration of central nervous system (CNS) axons.

The present invention pertains to an implantable device which eliminates or substantially reduces many of the disadvantages associated with prior art attempts at the regeneration of peripheral nerve and central white matter.

One aspect of the invention provides a medical device comprising
    a tubular body having a lumen and a long axis; and
    a plurality of silk elements laid substantially parallel along the long axis of the lumen of the tubular body.

The tubular body can comprise resorbable material. For example, a protein or protein-based material, which may be natural or synthetic. References to synthetic material include material synthesised by chemical processes as well as by recombinant DNA technology processes. A composite construction comprising fibres set in a matrix is preferred. The tubular walls of the device may be composed of silk fibres and a suitable protein material. For example, *Antherea pernyii* silk with a matrix of regenerated *Bombyx mori* protein.

The matrix can be formed from silk protein such as redissolved silk protein obtained from mulberry or non-mulberry silk worms, or natural silk fibroin obtained from mulberry or non-mulberry silk worms. For example, *Antherea pernyii* silk. The matrix can be stabilised by cross-linking such as by using formaldehyde gas, glutaraldehyde, citrate ions, ribose, glyoxal or genipin The fibres forming the body can comprise silk fibre that are helically laid or braided.

The silk elements in the lumen are preferably separated from each other at a distance between about 1 μm and about 100 μm.

Devices of the invention may suitably have a packing density of the silk elements in the range of from about 1 to about 30 per 10,000 μm$^2$, preferably about 1 to about 10 per 10,000 μm$^2$, or about 5 to about 10 per 10,000 μm$^2$.

In accordance with this aspect of the invention, the device may be composed of a tubular body with an external diameter of from about 1.0 to about 2.5 mm, preferably from about 1.5 mm to about 2.0 mm, or from about 1.0 mm to about 1.5 mm, most preferably about 1.4 mm or 1.5 mm.

The walls of the tubular body may have a thickness of from about 250 μm to about 750 μm, suitably from about 300 μm to about 600 μm, and values of around 300 to 350 μm may be preferred.

The length of the device may be from about 0.5 mm to about 150 mm. The length of the device may be chosen for suitability with the nerve to be repaired using the device. For example, where the device may be for the repair of smaller nerves, the device may be suitably of from about 1.0 mm to 5.0 mm, or 1.5 mm to 2.5 mm, or 1.0 mm to 2.0 mm. For the repair of larger size nerves, the device may be correspondingly larger, such as from about 10 mm to 20 mm. Autologous transplants of human nerves have successfully used lengths of 20 mm to 130 mm and devices of the invention may be similarly sized.

The silk elements may have a diameter of from about 5 μm to about 50 μm, suitably from about 10 to 20 μm.

In some preferred embodiments of the invention, the devices may be 2.0 mm long and have a diameter of 0.5 mm.

The silk elements or fibres used in the device can comprise mulberry silkworm silk, non-mulberry silkworm silk, spider dragline silk, and filaments spun from recombinant silk protein or protein analogues. Non-mulberry silkworms silk is particularly preferred. A suitable example is *Antherea pernyii* silk.

The silk elements are typically in the form of sliver silk or reeled silk or twisted silk. The silk elements may be conveniently arranged is a substantially longitudinal orientation with respect to the walls of the device.

To encourage cell migration, the silk elements preferably have a principal silk protein containing at least eight repeats of the triplet RGD, at least some of which are preferably located immediately adjacent to turns or predicted turns of the structure of the principal silk protein. The principal silk protein preferably has sites from which one or more arginine groups of the principal protein has been blocked to tune cell adhesiveness. The blocking can be achieved by one or more of deamination, sulfation, amide formation and blocking with cyclohexandione.

It may be convenient to use a blocking agent to produce a gradient in the density of free arginine groups from the distal to the proximal end of the device. This can be achieved by slowly and progressively lowering the device proximal end first into a solution of a blocking agent. Alternatively, a gradient of free arginine groups can be introduced into the silk elements before they are introduced into the lumen of the tubular body. Such a gradient can linear or non-linear. The gradient may encourage nerve cell processes to detach from the silk fibres at the proximal end of the device.

To encourage nerve cell processes to enter and leave the device it may be preferable to arrange the substantially longitudinally oriented silk elements so that they protrude 0.1 to 10 mm beyond one or both ends of the tubular body of the device lumen.

It is particularly preferred that the silk elements are set in a lumen matrix comprising a resorbable biocompatible polymer such as a hydrogel, for example alginate or hyaluronic acid with or without polylysine, or casein. Other components, such as extracellular matrix (ECM) may be present, such as fibronectin and/or laminin. These materials may be added to the lumen matrix in the conduit or coated onto the silk filaments in the lumen matrix.

A second aspect of the invention comprises a method of manufacturing a medical device comprising forming the tubular body and introducing the silk elements into the lumen of the tubular body so as to lie substantially parallel along the long axis of the lumen of the tubular body.

Formation of the tubular body can further comprise the steps of:
    preparing a former on which the tubular body is formed;
    laying down fibres on the former;
    applying a matrix to the fibres to form a composite body; and
    removing the former.

The formation of the tubular body can also comprise cross-linking the matrix.

It is also preferred to introduce a lumen matrix component between the silk elements within the lumen of the tube.

The silk elements may be washed with a solution of a chelating agent, for example, ethylene diamine tetra-acetic acid (EDTA) sodium salt to remove possible contaminants, such as transition metal ions which may be toxic. Other chelating agents could also be used. Preferably, the silk is degummed. This can be achieved by treatment of the silk using a protease, for example a subtilisin, but other mild proteolytic enzymes may also be used. The enzyme can then be washed out after treatment.

A third aspect of the invention provides a method for the regeneration of nerve cells comprising the implantation of a medical device according to the first aspect of the invention The present invention relates to an implantable device which can eliminate or substantially reduce many of the disadvantages associated with prior art attempts at the regeneration of peripheral nerve and central white matter.

More specifically the present device may be constructed from biocompatible, resorbable material whose ability to provide binding sites for growing nerve axons, Schwann cells and glial cells can be tuned.

The preferred form of a device according to present invention comprises a silk composite tube open at both ends and containing orientated silk filaments within its lumen. The wall of the composite tube typically has a substantially uniform thickness and, depending on the location into which it is to be implanted, a diameter ranging from 0.1 to 25 mm, preferably from 250 to 750 μm.

The silk composite tube typically comprises fine non-mulberry silk sliver filaments laid in a helical pattern with a crossing angle of approximately 55° and set in a matrix of regenerated that is redissolved silk fibroin obtained from mulberry or non-mulberry silk worms though it is to be understood that other resorbable biocompatible filaments and resorbable biocompatible matrices could be used instead. In a further embodiment the matrix is substantially composed of native silk fibroin extracted from the silk gland of mulberry or non-mulberry silkworms. The matrix is stabilized by covalent cross-links. In one embodiment this is achieved by treating with formaldehyde gas, but other cross-linking agents could be used. In a further embodiment a silk composite tube can be prepared from a braided silk tube prepared directly from 1 or 7-13 bave degummed non-mulberry silk using a braiding machine. The braided silk tube is treated with a solution of one or more resorbable biocompatible polymers such as regenerated mulberry or non-mulberry silk to form a matrix between the silk threads of the braided silk tube.

The silk composite tube contains non-mulberry silk filaments set in a lumen matrix containing hyaluronic acid (other lumen matrix materials include hydrogels such as hyaluronic acid with polylysine, alginate with or without polylysine and casein). The filaments are orientated substantially longitudinally with respect to the long axis of the silk composite tube and are cut off flush with the ends of the tube. In further embodiments the silk filaments and lumen matrix either extend a short distance beyond the ends of the tube or end a short distance short of the ends of the tube. The filaments are typically packed together in the lumen of the tube with a density of 1 to 10 filaments per 10,000 μm² giving an average spacing of approximately 30 to 100 μm between the filaments, but lower density packings can be used.

In a further embodiment, the device may additionally comprise one or more biologically active substances. The substances may be selected from the group consisting of growth factors, cytokines, antibiotics, immunosuppressants, steroids, non-steroidal anti-inflammatory drugs (NSAIDs). The growth factors may be nerve growth factors. For example, nerve growth factors may be added to the lumen matrix surrounding the filaments. A range of nerve growth factors can be used for this, including peripheral nerve NGF where the device is to be used to enhance the recovery of peripheral nerves or central nerve neurotrophin-3 (NT3) and brain derived neurotrophic factor (BDNF) where the device is to be used in the brain or spinal cord. It will be understood that other drugs or factors to promote nerve regeneration or to suppress the formation of glioma or fibrosis can be added to the lumen matrix surrounding the filaments. It is also to be noted that drugs and other factors to enhance the function of the device can also be added to the matrix of the silk composite tube. For example, antibiotics, immunosuppressants, steroid or non-steroid anti-inflammatory drugs (NSAIDs). Other biologically active substances include, but are not limited to, cAMP enhancers (such as rolipram or db-cAMP) to promote regeneration, molecules that reduce scar formation such as TFGβ antisera and/or chondroitinase, or molecules that reduce myelin inhibition, e.g. anti-Nogo treatments.

It is also envisaged that cells may be added to the devices of the invention, such as Schwann cells or olfactory ensheathing cells (OECs) to assist in myelination of nerve re-growth and/or neural stem cells. Other cell types could also be added as required. The cells may be endogenous cells from the patient into whom the device is to be implanted, or the cells may be exogenous cells from an external source, e.g. cells grown in culture. In other words, the cells may be autologous or non-autologous with respect to the immune system of patient.

Lengths of nerve conduit prepared according to the present invention can also be inserted into the brain or spinal cord with the aim of encouraging the repair of injured or degenerated white matter. They can be used in conjunction with cell seeding techniques with the aim of directing and encouraging implanted neurones, formed from implanted neuroblasts stem cells, to connect to appropriate parts of the central nervous system.

Where biologically active substances or cells are added to the devices of the invention, a concentration gradient (linear or non-linear) may be established with a higher concentration of substance or cells at one end (e.g. the proximal end) as opposed to the other end (e.g. the distal end) of the device. Alternatively a depot of substances or cells may be added to only one end of the device.

In a further embodiment the silk composite tube is omitted and orientated silk filaments set in a resorbable matrix are implanted directly.

For implantation an appropriate diameter device is selected according to the diameter of the nerve or white matter tract to be repaired. An appropriate length of the device is cut off with a sharp blade or other instrument. In one embodiment the device is held in place by one or more sutures. In another embodiment the device can be held in place with fibrin glue. The device can be implanted dry or can be soaked for five minutes to five hours in an appropriate physiological saline solution before use.

In accordance with the present invention, there is therefore provided a device as described above for use in the regeneration of nerve cells. Such devices may find particular application in the regeneration of nerve cells in the spinal cord or in a peripheral nerve.

The devices of the invention therefore find utility in the treatment of a trauma or an injury to a nerve or nerves in the body of an animal. The invention may therefore find application in both human medicine and in veterinary medicine. In humans the largest nerve is the sciatic nerve which is just under 20 mm in diameter at its largest point. The length of a suitable device for use in human medicine may vary but typically would be from about 10 mm to about 20 mm in view of clinically observed injuries to nerves requiring treatment.

The devices of the invention may therefore be useful in re-establishing connections between injured or damaged nerves in the central nervous system or in the peripheral nervous system. The invention provides for a means to reconstitute the nerve or spinal cord with an environment roughly similar to the cellular/extracellular environment that was present before the injury to the nerve. In the case of a peripheral nerve injury, that includes myelinating Schwann cells which are required for proper conduction of electrical impulses in axons and extracellular matrix molecules such as laminin, among other things. Devices of the present invention may therefore additionally comprise extracellular matrix components (ECMs), such as fibronectin and/or laminin, and also exogenous cells, such as Schwann cells.

The types of peripheral injuries that are treatable according to the present invention are those in which a nerve has been damaged in which transection of the nerve may have occurred. The injury may be described as neurotmesis. The clinical definition of such injuries is also referred to under the "Sunderland System" as either fourth-degree or fifth-degree neurotmesis. In fourth-degree neurotmesis, there is interruption of all neural and supporting elements, the epineurium may be intact and the nerve is enlarged. In fifth-degree neurotmesis, there is complete transection with a loss of continuity of the nerve.

Preferred features for the second and subsequent aspects of the invention are as for the first aspect *mutatis mutandis*.

The invention will now be further described by way of reference to the following Examples and Figures which are provided for the purposes of illustration only and are not to be construed as being limiting on the invention. Reference is made to a number of Figures in which.

PREPARATION OF THE DEVICES OF THE INVENTION

Preparation of the nerve regeneration conduits requires some or all of the following steps: preparation of former; laying fibres down on former; applying solutions of aqueous protein to form composite tubes; removal from former; wax removal; cross-linking the composite; introducing oriented silk filaments into tube; addition of matrix component between filaments within the lumen of the tube; introduction of extracellular matrix components such as fibronectin and/or laminin; introduction of nerve growth factors, pyrogen removal and sterilisation; addition of nerve growth factor(s); drying and cutting the device to length. Although the above order gives good results the order of certain steps is not crucial. For example cross-linking can be carried out after the addition of silk filaments to the tube; and pyrogen removal can take place before or after addition of NGF; NGF can be added before sterilisation if the latter is carried out by gamma irradiation.

Preparation of the Cylindrical Former

Formers are prepared as follows. The simplest method of preparing formers is to use stainless steel tubing or rods of appropriate diameters. These are cleaned and polished before use. The tubes can be readily slipped off the formers after the applied matrix material has been dried. For small diameter formers, a relatively stiff and straight wire is first coated in a thin layer of paraffin wax or some other material that melts at a relatively low temperature above ambient. Even coating can be achieved by dipping the wire vertically into molten wax. The outer diameter of the wax coating on the former defines the inner (luminal) diameter of the tube formed on it. Larger diameter formers up to 30 mm in diameter can be prepared by casting or machining rods of wax or coating a cylinder of appropriate diameter with wax. There are other methods of preparing formers which can be removed from within the lumen of a silk tube formed around them that are readily available to workers in this field.

Laying Fibres Down on the Former

Three types of silk filament are preferably used for the fibre reinforcing in the walls of the tubes that form the outer wall of the nerve regeneration conduits: silk sliver (combed out and carded degummed filaments from cocoon waste); degummed single bave silk prepared from silk reeled from one cocoon at a time; degummed 7-13 bave 20-37 denier silk prepared from silk reeled from 7-13 cocoons at a time. Tussah silk from *Antheraea pernyi* has been used but any mulberry or non-mulberry silk or silk filament extruded from natural, recombinant or regenerated silk protein could be used instead.

Degummed 7-13 bave 20-37 denier silk gave good results. The silk is first washed with a dilute solution of ethylene diamine tetra-acetic acid (EDTA) sodium salt to remove possible contaminants, such as transition metal ions which may be toxic. Other chelating agents could also be used. Preferably, the silk is degummed. This is achieved by treatment of the silk using a protease, for example a subtilisin, but other mild proteolytic enzymes may also be used. The enzyme is washed out after treatment.

Tussah silk sliver contains a large number of fine parallel filaments which also gave good results. The parallel filaments can be gripped between thumb and finger and wound around the former to provide a helical lay with a crossing angle between 40 and 50 degrees. A winding device can be used to mechanise this procedure. Alternatively the single or 7-13 bave silk threads can be wound in a helical fashion onto the former. For continuous silk filaments a simple device can be used to wind a helical lay onto the former. This uses a small electric motor to drive a slowly rotating cylindrical former and an eccentric cam whose cam follower distributes the silk on the former. Devices for winding silk filaments continuously on to a flexible cylindrical former are easily constructed.

As an alternative a braided tube can be prepared directly from 1 or 7-13 bave degummed silk using a braiding machine The braided tube can be used to form the silk composite tube as is described below.

Applying Solutions of Aqueous Protein to Form Composite Tubes

A variety of proteins can be used to supply the matrix of the silk composite. Good results have been obtained with concentrated 10-40% w/v solutions of freshly prepared regenerated Bombyx mori fibroin prepared by dissolving commercial fibroin powder in aqueous 6.3 M lithium bromide solution. The lithium bromide is removed by exhaustive dialysis against distilled water at 4° C. The dialysate is concentrated within the dialysis tubes by evaporation or reverse dialysis. The resulting regenerated fibroin solution is painted on to the silk threads while they are still on the former to produce a tube without pores. The fibroin solution is allowed to dry. The resulting regenerated silk/Antheraea silk composite tube is now ready to be removed from the former. The composite can also be formed by spraying regenerated fibroin solution or dipping the former into the same solution. Concentrated fibroin solutions taken directly from the silk worms of mulberry or non-mulberry silk worms can be used in place of regenerated fibroin. A plurality of proteins can also be used instead of regenerated fibroin. These include fibroin glue, dilute solutions of gelatine, or serum albumen. Other water soluble proteins, hyaluronic acid or other biocompatible polymers could be used instead. Alternatively instead of using a silk lay on a former, a tube of braided silk can be coated with the matrix protein or other polymer solution by spraying or dipping.

Removal from Former

Where a stainless steel former is used, the silk composite tube can be easily removed by sliding it off the former. For narrow composite tubes, this can be achieved with fine forceps. Where a wax coated former is used, the composite silk tube is removed from this by gently melting the wax or other low melting point coating to the former. Alternatively a former whose diameter can be reduced can be used, for example by removing a central core, before sliding it out of the silk composite tube surrounding it.

Removal of Wax

Where wax has been used traces of this remaining on the composite silk tube can be removed by soaking in benzene, xylene or other wax solvent.

Cross-Linking the Composite

The following procedure can be used for cross-linking the matrix protein of the silk composite tube. Excess dry paraformaldehyde is placed in the bottom of a sealable container and 0.2 ml of distilled water are added to 2 gram of paraformaldehyde in a 0.5 liter container. The paraformaldehyde is covered by a filter paper and the silk composite tubes are placed on top of this. After sealing the container it is heated for one hour to 80° C. After cooling the silk tubes are removed from the container and washed exhaustively with warm water.

Introducing Oriented Silk Filaments into Tube

Filaments of silk sliver are introduced into dry silk composite tubes as follows. A suitable sized needle or bodkin is first threaded with silk sliver. A sack needle is useful for the larger diameter silk composite tubes. Typically the filaments are then painted with a fairly viscous hyaluronic acid solution. The threaded needle or bodkin is pushed through the silk composite tube to fill it with oriented silk filaments under which conditions excess hyaluronic acid oozes out of the cut end of the tube. Other resorbable gels could be used in place of hyaluronic acid. In one embodiment the use of hyaluronic acid or other resorbable gels is omitted. If required threaded needles are pushed repeatedly through the silk composite tube until the appropriate packing density of silk sliver filaments is achieved within the lumen of the tube. With experience this can be judged by eye. Alternatively an accurate measure of the density of packing of silk filaments into the tube can be obtained as follows: A measured length of silk composite tube is weighed and reweighed after introducing silk filaments and cutting them off flush with the ends of the tube. Filaments can be added to or removed from the tube until the desired weight of filaments are in the lumen of the tube. A stereomicroscope fitted with a squared eyepiece graticule is used to measure the number of filaments per square mm cross sectional area of the tube. Scanning electron microscopy before experimental implantation indicates that a packing density of 10 to 1 filaments per 10,000 $\mu m^2$ giving an average spacing of approximately 30 to 100 $\mu m$ between the filaments is best.

Addition of Matrix Component Between Filaments within the Lumen of the Tube

Lumen matrix components between the silk filaments are used to hold the filaments in position during all subsequent stages in device preparation and insertion while maintaining a suitable separation between the filaments by forming a hydrogel. They also enhance nerve growth into the device. A variety of biological macromolecules can be used to provide the lumen matrix between filaments. These hydrogels include hyaluronic acid with or without polylysine, alginate with or without polylysine, casein, fibrin glue, serum albumen, and gelatine. Aqueous solutions of these macromolecules are prepared using warming where necessary. Other solvents can be used instead of water. Silk composite tubes containing orientated silk filaments within their lumen are immersed in a solution containing one or more of these polymers. A vacuum can be applied to assist infiltration. In the case of fibrin glue the silk composite tubes containing orientated silk filaments are first infiltrated with fibrin solution and then with a thrombin solution to initiate the formation of the fibrin glue.

Pyrogen Removal and Sterilisation

Pyrogen removal is best carried out before adding nerve growth factors. It is best carried out by washing with aqueous 1% v/v dimethyl sulfoxide containing a final concentration of 0.1% v/v Tween 20™. Two to five washes are usually carried out with this solution. After pyrogen removal the devices can be washed in sterile and pyrogen-free physiological saline. All glass or plastic wear or other laboratory equipment coming in contact with the solutions used for pyrogen removal should be baked at 240° C. for at least two hours to remove pyrogens.

Introduction of Biologically Active Substances Such as Nerve Growth Factors (NGF(s))

A range of biologically active substances such as nerve growth factors can be introduced into the device. These include peripheral nerve NGF where the device is to be used to enhance the recovery of peripheral nerves or central nerve neurotrophin-3 (NT3) and brain derived neurotrophic factor (BDNF) where the device is to be used in brain or spinal cord. Nerve growth factors are best added while forming the lumen matrix component between the filaments. They can be mixed with the lumen matrix solution before it is added to the silk composite tube containing oriented silk filaments within its lumen.

Drying and Cutting the Device to Length

The device is first blotted to remove excess solution before being dried. A plurality of drying methods can be used including air drying or freeze drying. Suitable lengths of the conduit are best cut from the dried device. These can be implanted directly or rehydrated in sterile and pyrogen-free 0.9% w/v saline before implantation.

Implantation of the Devices

For the treatment of spinal transections or partial transections discs of the device 2 to 10 mm thick are cut from lengths of the prepared silk composite tubes 2-20 mm in diameter containing silk filaments. These are inserted transversely into the spinal cord at the site of injury. In the case of avulsion injuries, a conduit can be inserted to connect the spinal cord with the avulsed root(s).

A conduit for encouraging the regeneration of peripheral nerves is prepared from narrower tubes 1-15 mm in diameter, the diameter depending on the size and location of the nerve to be repaired. The devices should be lightly sutured into position.

Lengths of nerve conduit can also be inserted into the brain with the aim of encouraging the repair of injured or degenerated white matter. They can be used in conjunction with cell seeding techniques with the aim of directing and encouraging implanted neurones, formed from implanted neuroblasts stem cells, to connect to appropriate parts of the central nervous system. Cell seeding techniques can also be used with spinal cord or peripheral nerve implants.

The device described above offers four advantages over the prior art.

First the device has superior tensile properties for the following reasons. These arise from the exceptionally strong non-mulberry silk which can be used for both the silk composite tube and the composite nature of the tube and the contents of its lumen. In addition the helical lay of fibres in the tube is designed to provide both longitudinal and radial strength and toughness to the tube. Also the body of the device is further toughened by its composite construction.

Second, the design of the device enables the migration of axons through the device to be optimised. This is because the density of packing of the silk filaments and hence the dimensions of the channels between them can be readily tuned. Further the non-mulberry silks used in the device naturally carry multiple repeats (preferably at least eight) of the cell adhesion sequence RGD to which cells including axons bind. At least some of the repeats are located adjacent to a turn or a predicted turn of the protein. Furthermore it is to be understood that for axonal migration the density of the binding sites needs to be carefully controlled. If the density of accessible RGD sites is too large the axonal outgrowths bind too tightly to the silk fibres and do not emerge from the opposite end of the device. On the other hand if the density of the accessible RGD sites is too small, the adhesion of the axonal outgrowths to the silk filaments is insufficient and their ability to migrate into the device is reduced. The binding of axonal outgrowths to the silk filaments can therefore be tuned by varying the density of the RGD sites on the silk filaments. This can be achieved in two ways. The natural density of the RGD sites varies from species to species ranging from one per silk molecule to more than twelve per molecule. Thus a silk can be selected with an appropriate density of RGD sites. The natural density of RGD groups in *Antheraea penzyii* silk gives good results. In addition it would be possible to further tune the density of RGD groups by partially substituting the arginine epsilon amino groups with mild blocking as will be understood by a person skilled in the arts. Methods include but are not limited to sulfation and amide formation. The groups can also be blocked by cyclohexandione.

Third, the device is stiff when dry and plasticizes when wet to give bending and tensile properties which resemble those of natural nerves. The stiffness when dry or partially hydrated is very helpful when inserting the device and suturing it into position while the flexibility when wet mimics that of natural nerve.

Fourth, the hyaluronic acid gel within the lumen matrix when the device is dry helps to hold in place the silk filaments within the lumen making it easy to cut off and handle the desired length of the device without loss or disorientation of the fine silk filaments within the lumen of the device. Further, the hyaluronic acid when hydrated stimulates neuronal ingrowth.

EXAMPLE 1

Dissociated DRGs/Silk in Culture

Initial in vitro experiments demonstrated that *Antherea pernyii* silk fibres in culture support neurite outgrowth by peripheral nervous system (PNS) neurons (dorsal root ganglion cells) and also support the adherence and migration of PNS support cells (Schwann cells). Experiments were carried out using both rat neonatal (P3) dorsal root ganglion (DRG) and sciatic nerve explants and rat adult dissociated DRG cells.

Methods

Adult or neonatal (P3) rats were sacrificed by inhalation of high concentration of $CO_2$, and DRG neurons were cultured using published procedures (Huang et al Neuroreport 16: 89-93 (2005)) in accordance with the UK Animals (Scientific Procedures) Act. Dorsal root ganglia were removed and cleaned before being dissociated chemically (0.125% collagenase, 2h; Sigma, UK) and mechanically in Bottenstein and Sato's serum-free medium (BSF-2; containing 0.3% bovine serum albumin (BSA), 1% N-2 supplement and 100 unit ml-1 penicillin/100 µg ml-1 streptomycin in Ham's F-12 basal medium; all reagents from Life Technologies, USA). The cell suspension was then centrifuged at 600 rpm for 5 min followed by resuspension and a second centrifuge through a 15% BSA cushion at 900 rpm for 10 min. Pelleted cells were resuspended in BSF-2 and then seeded at a density of 900-1000 neurons/coverslip onto glass coverslips with attached silk fibres. Cultures were maintained in BSF-2 plus 100 ng/ml nerve growth factor (NGF) for 7 days at 37° C. in a humidified atmosphere of 95% air and 5% $CO_2$. Coverslips were prepared by first coating with poly-L-lysine (100 µg/ml) and rat tail collagen and then letting the silk fibres adhere to the collagen. In some cases, coverslips with adherent silk fibres were coated in 10 µg/ml laminin prior to seeding with DRG cells. In addition, in some experiments DRG and sciatic nerve explants were used instead of dissociated DRG cells. In such cases neonatal (P3) rats were sacrificed by inhalation of high concentration of $CO_2$, and lumbar dorsal root ganglia and segments of sciatic nerve were excised, attached to poly-L-lysine and collagen coated coverslips which had attached laminin-coated silk fibres, and cultured in BSF-2 plus NGF for 7-10 days.

At the end of the culture period, cultures were fixed in 100% methanol or in 4% paraformaldehyde and labelled with the following reagents: mouse βIII tubulin (1:1000) to reveal DRG cell bodies and processes, rabbit GAP-43 antibody (1:1000) to reveal regenerating DRG processes and the processes of non-myelinating Schwann cells, rabbit S100 antibody (1:1000) to reveal Schwann cells, and Hoechst 3342 (2 µg/ml) as a general nuclear counterstain. Primary antisera were visualized using anti-rabbit TRITC (tetramethylrhodamine isothiocyanate) and anti-mouse FITC (fluorescein isothiocyanate) secondary antisera. Preparations were then examined on a Zeiss LSM-510 confocal microscope.

RESULTS

Neonatal DRG and Sciatic Nerve Explants

Figure 1:
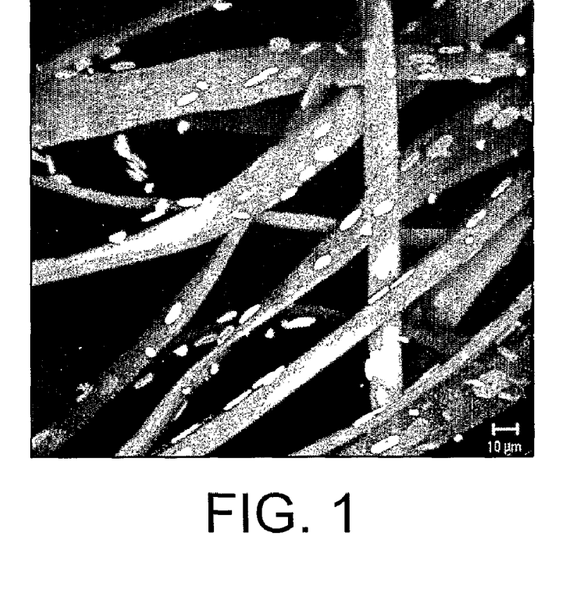
FIG. 1 shows dorsal root ganglion (DRG) explants with Hoechst staining of Schwann cell nuclei, indicating that many Schwann cells had migrated out of the explants and adhered to silk fibres.
Figure 2:
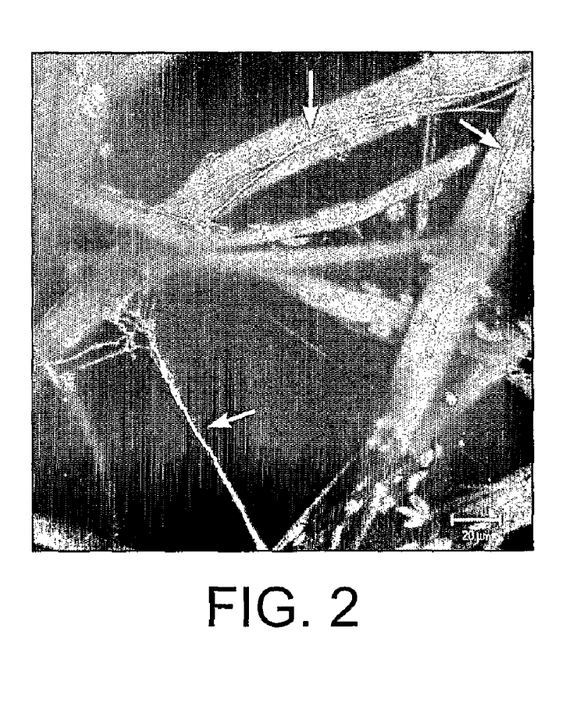
FIG. 2 also shows DRG explants with Hoechst staining indicating that many Schwann cells had migrated out of the explants and adhered to silk fibres. In addition, GAP-43 immunoreactive neurites (arrows) are seen to extend along individual silk fibres and in some cases also to bridge individual fibres.

In DRG explants (FIGS. 1,2), Hoechst staining indicated that many Schwann cells had migrated out of the explants and adhered to silk fibres. In addition, GAP-43 immunoreactive neurites could clearly be seen to extend along individual silk fibres and in some cases also to bridge individual fibres.

Figure 3:
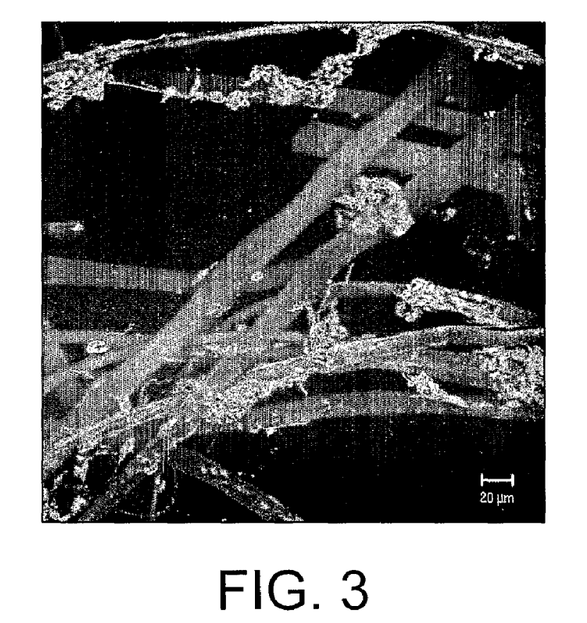
FIG. 3 shows sciatic nerve explants with Hoechst labelled and GAP-43 immunoreactive Schwann cells seen to have migrated out of the explants and adhered to silk fibres.

In sciatic nerve explants (FIG. 3), many Hoechst labelled and GAP-43 immunoreactive Schwann cells had migrated out of the explants and adhered to silk fibres, confirming that the fibres provide a very good substrate for Schwann cell attachment.

Dissociated Adult DRG Cells

Figure 4:
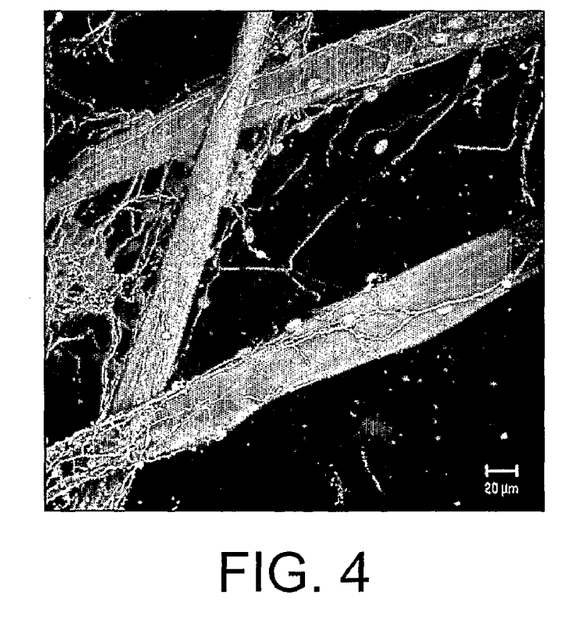
FIG. 4 shows adult DRG cultures with Hoechst-labelled Schwann cell nuclei and GAP-43 immunoreactive neurites shown adhering to individual silk fibres where the silk had been coated with laminin
Figure 5:
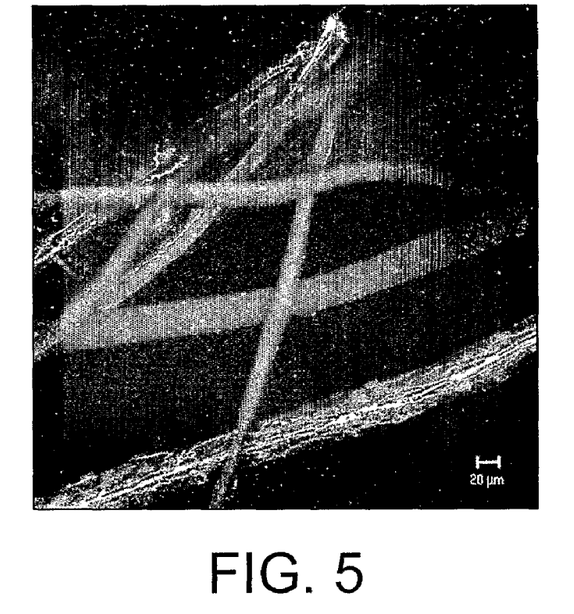
FIG. 5 shows adult DRG cultures with Hoechst-labelled Schwann cell nuclei and GAP-43 immunoreactive neurites shown adhering to individual silk fibres where the silk had not been coated with laminin

In adult DRG cultures (FIG. 4) many Hoechst-labelled Schwann cell nuclei and GAP-43 immunoreactive neurites were observed adhering to individual silk fibres, confirming that the fibres also support the growth of adult PNS neurons and supporting glial cells. Extensive growth was seen both in cultures in which the silk had been coated with laminin (FIG. 4) and in cultures without laminin (FIG. 5), confirming that the silk itself is a good substrate for neuronal growth and does not need an additional extracellular matrix coating.

Figure 6:
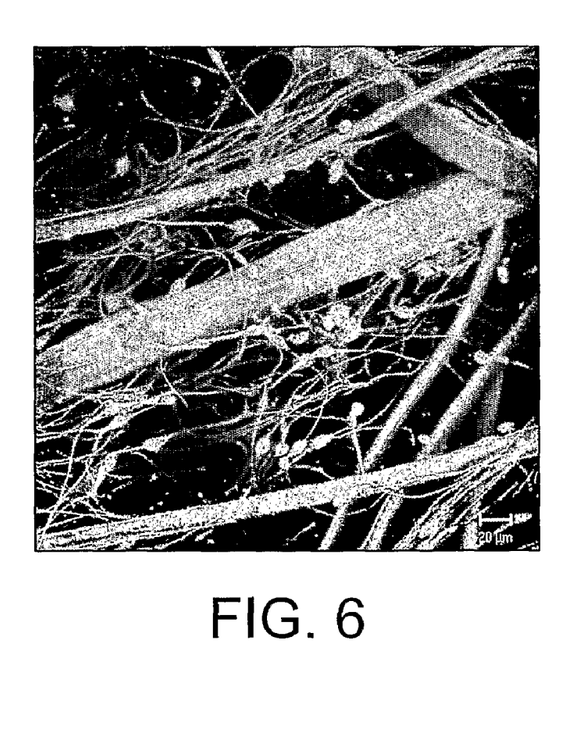
FIG. 6 shows labelling of cells using the glial-specific marker S100 which demonstrates that many S100 immunoreactive Schwann cells were associated with the silk fibres.
Figure 7:
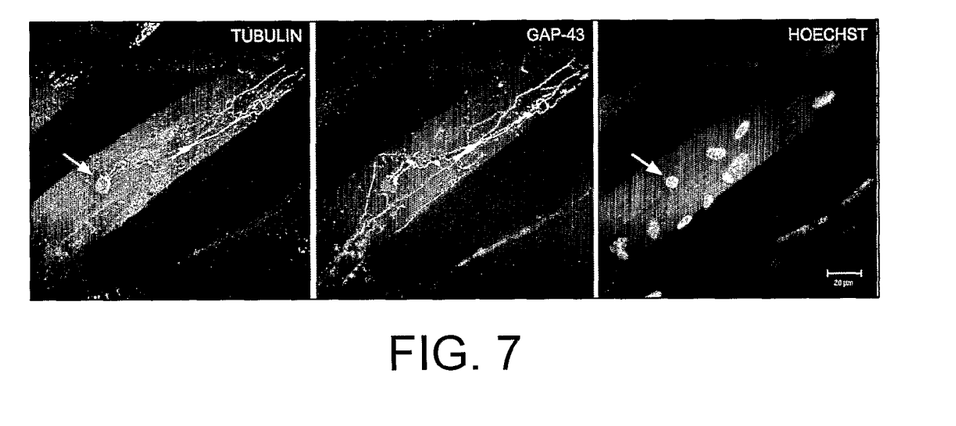
FIG. 7 shows labelling of cells using GAP-43 and the neuron-specific marker βIII tubulin which demonstrates that some of the Hoechst-labelled nuclei (arrows) and the fine GAP-43 immunoreactive processes are neuronal in origin.

In order to further characterize the growth observed in vitro, labelling was carried out using the glial-specific marker S100 and the neuron-specific marker βIII tubulin. This confirmed that many S100 immunoreactive Schwann cells were associated with the silk fibres (FIG. 6), and that the fine GAP-43 immunoreactive processes were neuronal in origin (FIG. 7). Most Hoechst nuclei are oval, tubulin-negative, and belong to Schwann cells. However some are round and tubulin-immunoreactive (arrow in FIG. 7), and extend tubulin and GAP-43 immunoreactive neuronal processes along the silk. These are DRG neurons which have adhered to the silk and extended processes along the silk, supported by associated Schwann cells.

Studies in vitro demonstrate that fibres made from silk support axonal growth by both neonatal and adult PNS neurons (DRG cells) and also support the attachment and migration of Schwann cells. This is an important property, because the Schwann cells are known to assist axonal growth.

EXAMPLE 2

Implantation of Silk Fibres into the Adult Rat Spinal Cord.

Initial in vivo experiments were undertaken to examine the effects of implanting silk fibres into the spinal cord. Of particular interest was the degree and orientation of axonal growth (relative to the silk fibres) as well as the effects of the implants on the surrounding intact nervous tissue (i.e. the degree of necrosis and the inflammatory response).

Methods: Initial in vivo experiments on silk implanted into the spinal cord took place on bundles of silk fibres that were unbound (i.e. not contained within a conduit). Animal care and procedures were carried out in accordance with guidelines and protocols approved by the United Kingdom Home Office. Young adult male Wistar rats were anesthetized with halothane (4% induction, 2% maintenance). The skin and muscle overlying the spinal column were incised and a laminectomy was performed between the T7 and T9 levels. The dura mater was opened and a portion of the spinal cord approximately 2 mm long that extended approximately 0.5 mm laterally from the midline and 1 mm ventrally from the surface of the spinal cord was removed using iris scissors. A bundle of silk fibres was then placed into the lesion cavity with the orientation of the silk fibres parallel to the longitudinal axis of the spinal cord. The lesion site was then covered with gelfoam and the overlying muscle and skin sutured. Animals survived for between 1 and 8 weeks following implantation. After the appropriate survival time, animals were deeply anesthetized with sodium pentobarbital (Sagatal, RMB, 60 mg/kg) and perfused through the ascending aorta with 50 ml of 0.01M phosphate-buffered saline (PBS) followed by 4% paraformaldehyde in 0.01M phosphate buffer, pH 7.4. The spinal cord was dissected, postfixed in 4% paraformaldehyde for 1-2 h, and cryoprotected in 15% sucrose in PBS overnight. Longitudinal sections 10-12 mm in thickness were taken through the implant site.

Sections containing the implant site were then processed for immunohistochemistry. Axonal ingrowth was characterized using an antibody to protein gene product 9.5 (PGP9.5), while an antibody to the low-affinity p75 receptor was used to label Schwann cells infiltrating the implant site. In addition, an antibody to macrophages (ED1) was used to begin to characterize the inflammatory reaction to the implants while an antibody to the astrocyte marker glial fibrillary acid protein (GFAP) was used to assess the glial reaction in the intact tissue surrounding the implant. The general procedure for immunohistochemistry was as follows: a 48 hour incubation in primary antibody, two ten minute washes in phosphate buffered saline, a 2-h incubation in secondary antibody conjugated to tetramethyl rhodamine isothiocyanate (TRITC) or fluorescein isothiocyanate (FITC) (both from Jackson Immunoresearch Laboratories Inc.). Following three more 10-min washes, slides were either coverslipped in PBS glycerol (1:3) containing 2.5% 1,4-diazobicyclo-(2.2.2)-octane or processed for immunohistochemistry to a second antibody in an identical fashion to that described above.

Figure 8:
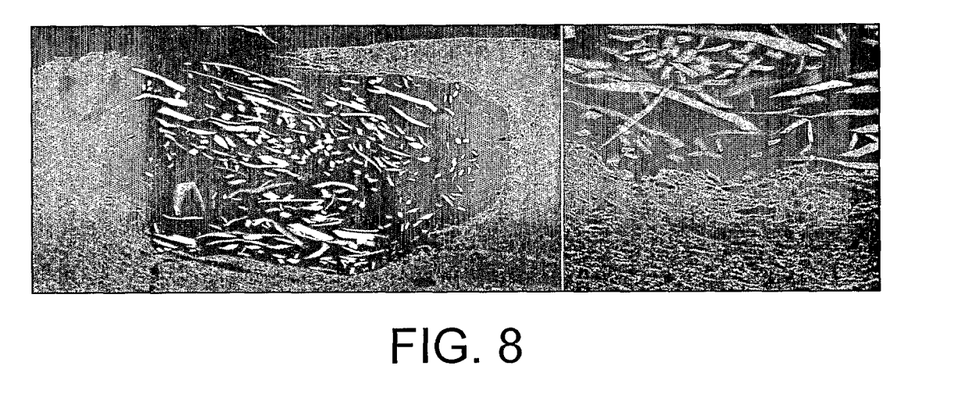
FIG. 8 shows silk fibres and the spinal cord (white fibres, FIG. 8, left). Labelling with the astrocyte marker GFAP showed that in general the silk fibres were in close proximity to the adjacent intact spinal cord (FIG. 8, right) with little or no necrotic tissue between the host spinal cord and the implant.

Silk fibres autofluoresced and could clearly be seen in the spinal cord (white fibres, FIG. 8, left). Labelling with the astrocyte marker GFAP showed that in general the silk fibres were in close proximity to the adjacent intact spinal cord (FIG. 8, right) with little or no necrotic tissue between the host spinal cord and the implant. In addition, the astrocytic reaction was typical of that seen for spinal cord damage. Both of these features indicate that silk fibres are well tolerated by the spinal cord.

Figure 9:
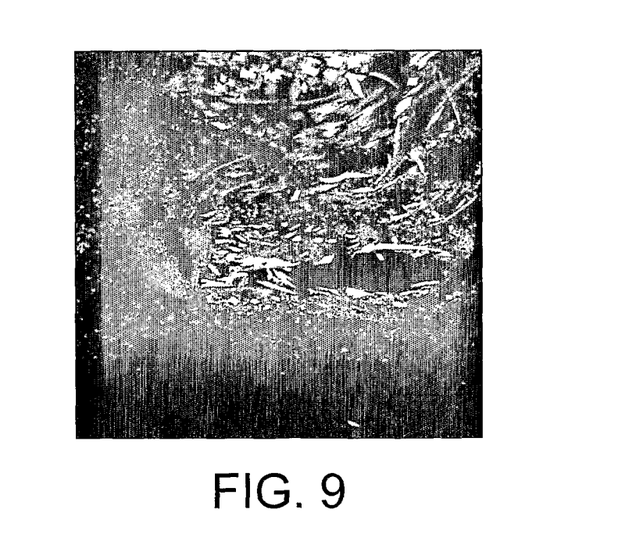
FIG. 9 shows macrophage infiltration within the bundle of silk fibres implanted into the spinal cord as well as the surrounding tissue.

Macrophage infiltration was seen (FIG. 9) within the bundle of silk fibres implanted into the spinal cord as well as the surrounding tissue. The degree of this infiltration progressively diminished and generally few macrophages were seen more than 2 mm from the implant. This level of inflammatory response compares favourably with other implants used (e.g. fibronectin) as well as the inflammatory response following spinal cord injury without treatment, further indicating good compatibility of the silk fibres with the host spinal cord.

Figure 10:
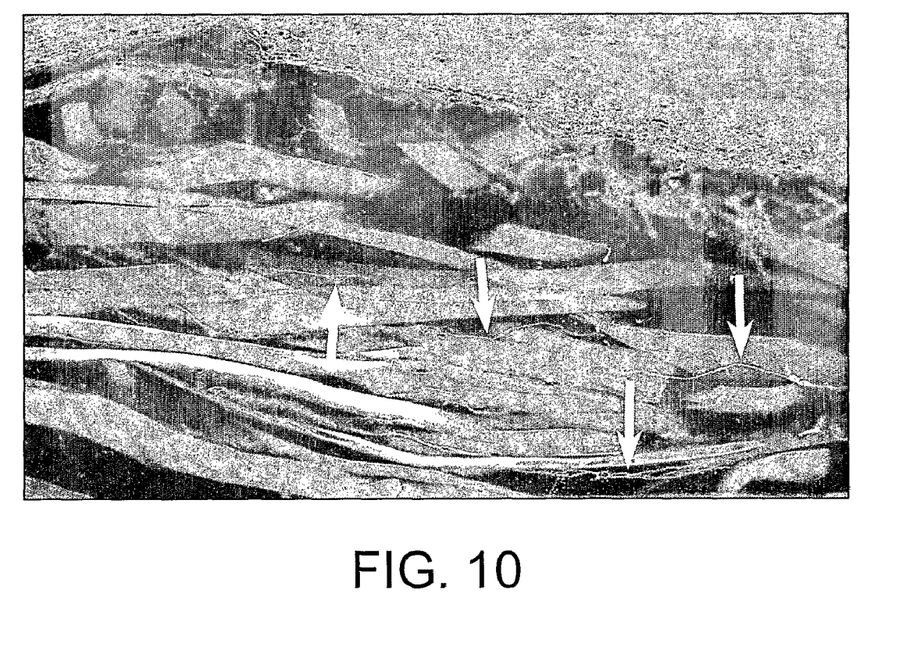
FIG. 10 shows labelling with the axonal marker PGP 9.5 of axons (arrows) growing into the silk implant with orientation parallel with that of the silk fibres.

Labelling with the axonal marker PGP 9.5 (FIG. 10 showed that numerous axons (shown by arrows) grew into the silk implant and in general showed an orientation parallel with that of the silk fibres. Maximal growth was seen 4 weeks following implantation (the latest time point examined).

Figure 11:
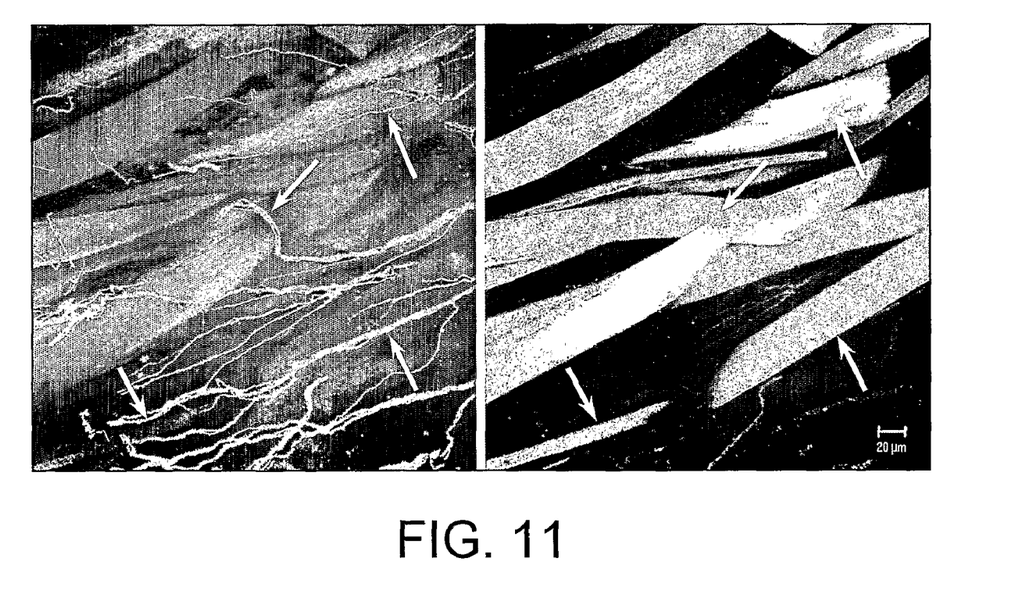
FIG. 11 shows confocal microscopy of PGP 9.5 labelled axons growing along as well as between individual silk fibres. The left hand panel shows axons marked with arrows and the right hand panel shows silk fibres marked by arrows.

Confocal microscopy (FIG. 11) further showed that PGP 9.5 labelled axons grew along as well as between individual silk fibres. In addition, there was no indication of any degradation of the silk fibres by this time point (4 weeks)

Figure 12:
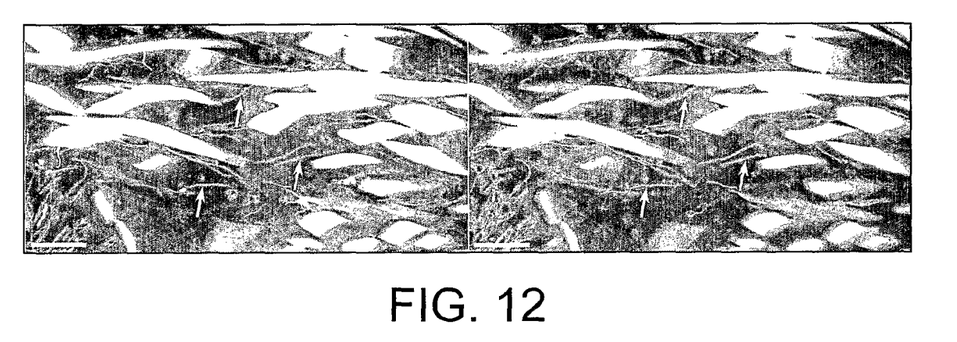
FIG. 12 shows double labelling with the axonal marker PGP 9.5 and the Schwann cell marker p75. The left hand panel shows axons and the right hand panel shows Schwann cells.

FIG. 12 shows double labelling with the axonal marker PGP 9.5 and the Schwann cell marker p75 and reveals a close correspondence between Schwann cell and axons that have grown into the mat. This suggests that much of the growth seen in implants may be of peripheral origin and/or is stimulated by the well established neurotrophic support associated with Schwann cells

EXAMPLE 3

Implantation of Silk Fibres within a Silk Conduit (First Iteration).

Figure 13:
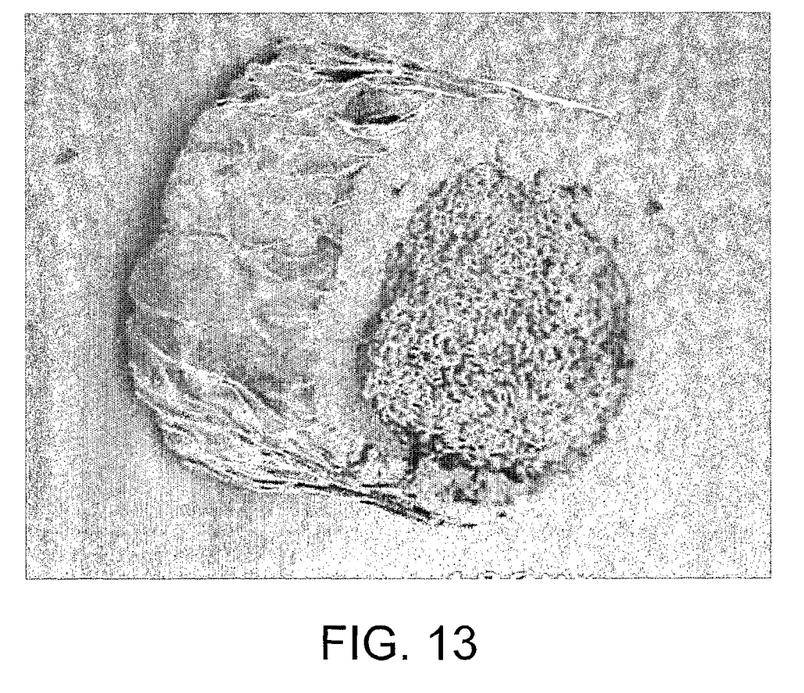
FIG. 13 shows a conduit of silk fibres arranged within the core of the conduit.

Initial investigations into the use of a silk based conduit in the spinal cord examined a conduit composed of a silk conduit with tightly packed silk fibres within the core (FIG. 13).

Methods: Implantation methods were identical to that described in (2) above with the exception that the diameter of the implant (approximately 1 mm) required a slightly wider lesion cavity be made in the spinal cord.

Results: Results indicated that these implants did not integrate into the spinal cord and fell out of the spinal cord during tissue removal. This was likely to be due to the packing density of the fibres within the conduit being too great to allow for penetration of any endogenous elements into the implant, thus making any sort of integration with the host spinal cord impossible. It is, however, important to note that the lesion cavity was essentially the same size as the implant in all animals and the spinal cord around the implant site had no indication of necrosis, indicating that these implants had been well tolerated by the host spinal cord.

EXAMPLE 4

Implantation of Silk Fibres within a Silk Conduit Containing Hyaluronic Acid

Failure to see integration of silk conduits (see above) suggested that silk fibres within the core of the conduit would require fibres to be suspended in a biodegradable medium that would allow space for infiltration of axons and other endogenous elements but also be permissive for axonal growth. A conduit consisting of a silk outer sheath with silk fibres suspended in hyaluronic acid was therefore implanted in the core.

Methods: Implantation and staining methods were identical to that described in (Example 3) above with the exception that the diameter of the implant (approximately 1 mm) required a slightly wider lesion cavity to be made in the spinal cord.

Figure 14:
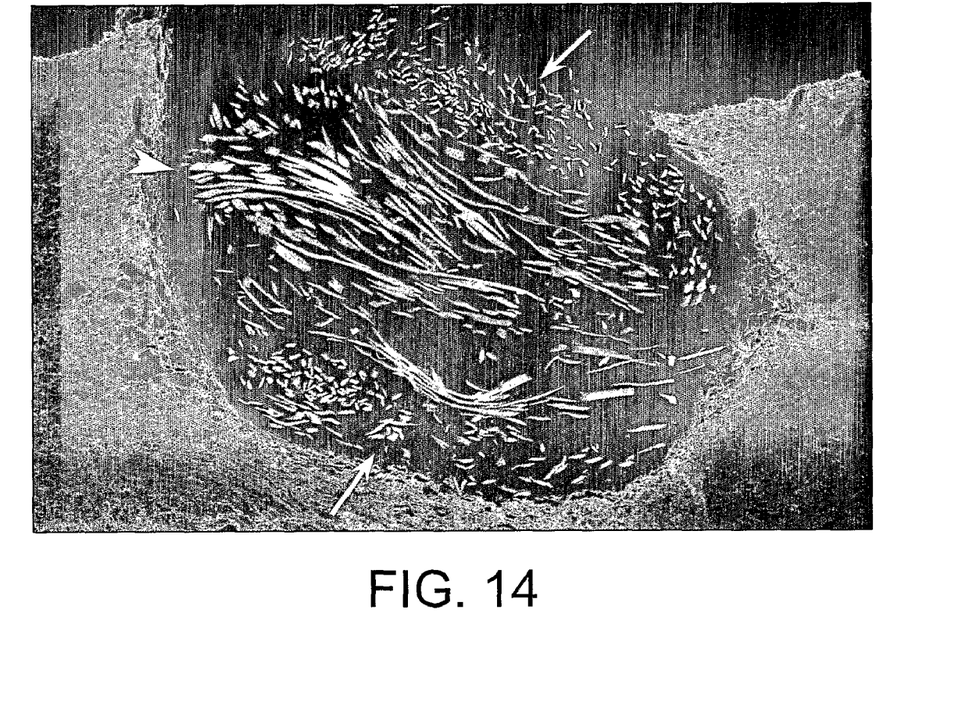
FIG. 14 shows the structure of a conduit implanted into spinal cord, with each wall of the outer sheath appearing as a strip of small silk fragments (arrows) and the inner core as longitudinally oriented strands (arrowhead).
Figure 15:
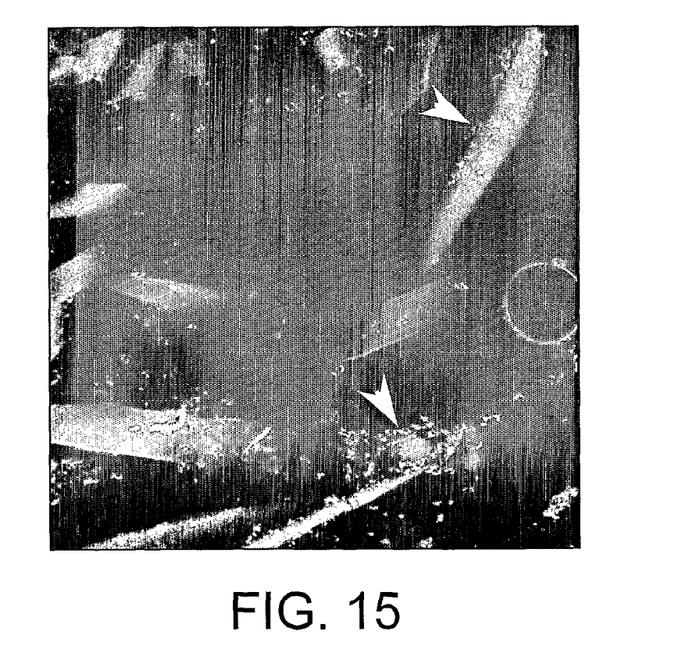
FIG. 15 shows macrophage infiltration into silk conduits was similar in appearance and degree to that seen with unbound silk fibres (see FIG. 9). In addition, by 8 weeks post-implantation, macrophages could be seen clustering around individual silk fibres.

Results: The structure of the conduit was clearly visible (FIG. 14), with each wall of the outer sheath appearing as a strip of small silk fragments (arrows) and the inner core as longitudinally oriented strands (arrowhead). As with the unbound silk (see section 2), GFAP labelling showed that the silk implant was well integrated into the host spinal cord with little or no necrotic tissue between the astrocytic scar and the implant Macrophage infiltration into silk conduits was similar in appearance and degree to that seen with unbound silk fibres (FIG. 15) compared to FIG. 9. In addition, by 8 weeks post-implantation, macrophages could be seen clustering around individual silk fibres, although there was still no evidence that silk fibres had begun to break down.

Figure 16:
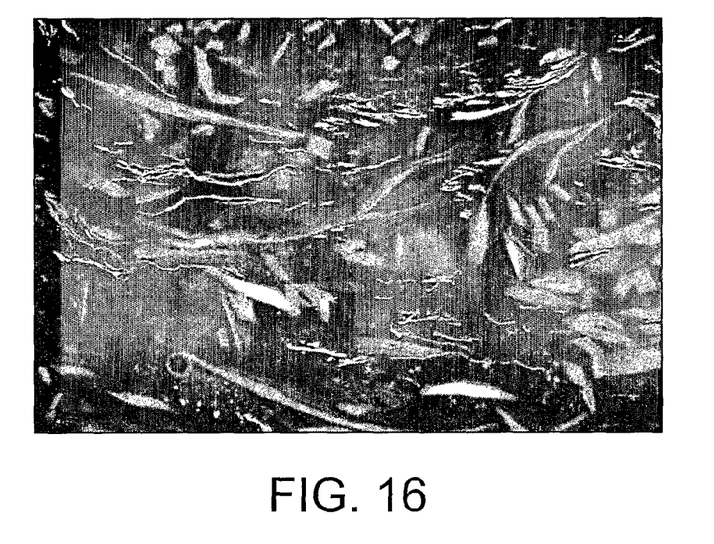
FIG. 16 shows PGP 9.5 stained axons growing between silk fibres.

As with unbound silk (see Example 3) numerous PGP 9.5 stained axons could be seen growing between silk fibres (see FIG. 16). In contrast to the unbound silk fibres, many of the ingrowing axons could be seen growing in fasicles.

Figure 17:
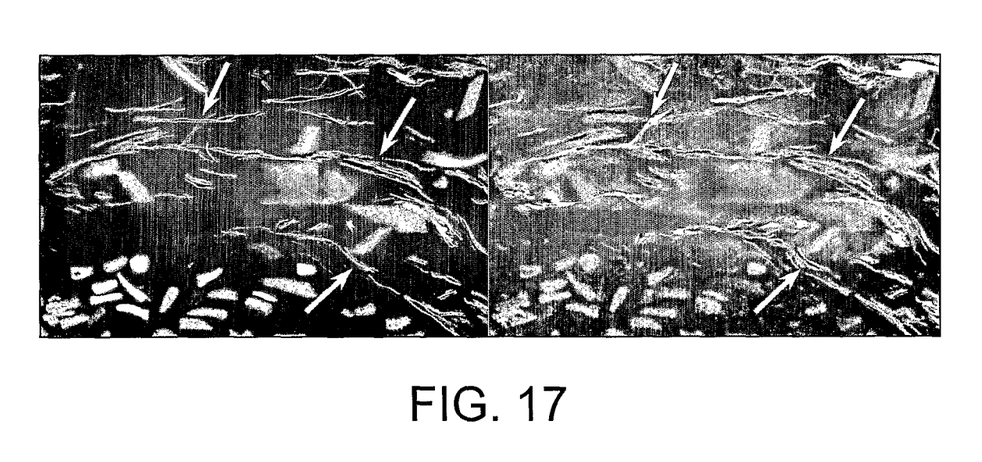
FIG. 17 shows that double labelling with the axonal marker PGP 9.5 and the Schwann cell marker p75 showed a close correspondence between Schwann cell and axons that have grown into the mat. The left hand panel shows axons and the right hand panel shows Schwann cells.
Figure 18:
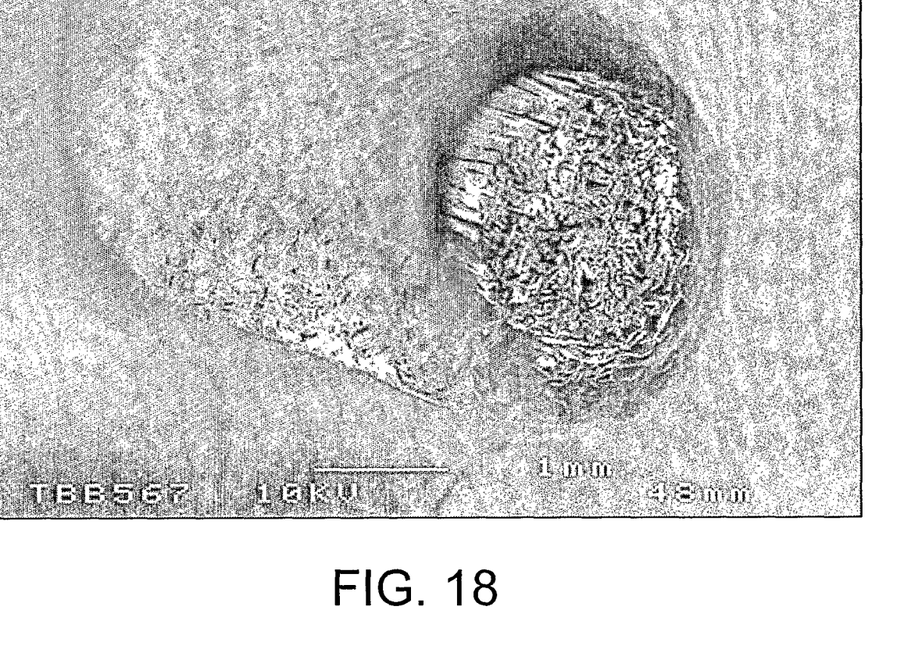
FIG. 18 shows a scanning electron micrograph of the nerve conduit according to one embodiment of the invention.

In addition, as with unbound silk (see Example 2) double labelling with the axonal marker PGP 9.5 and the Schwann cell marker p75 showed a close correspondence between Schwann cell and axons that have grown into the mat (FIG. 17).

The invention claimed is:

1. A medical device for regeneration of nerve cells comprising
a tubular body having a lumen and a long axis; and
a plurality of silk elements laid substantially parallel to the long axis of the lumen of the tubular body.
2. A device as claimed in claim 1, wherein the tubular body comprises resorbable material.
3. A device as claimed in claim 1, wherein the body has a composite construction comprising fibers set in a matrix.
4. A device as claimed in claim 3, wherein the matrix is silk protein.
5. A device as claimed in claim 4, wherein the silk protein is redissolved silk protein obtained from mulberry or non-mulberry silk worms, or natural silk fibroin obtained from mulberry or non-mulberry silk worms.
6. A device as claimed in claim 4, wherein the matrix has been stabilized by cross-linking.
7. A device as claimed in claim 6, wherein the cross-linking has been achieved using formaldehyde gas, citrate ions, ribose, glyoxal or genipin.
8. A device as claimed in claim 3, wherein the fibers forming the body are helically laid or braided.

9. A device as claimed in claim 3, wherein the fibers forming the body are silk fibers.

10. A device as claimed in claim 1, wherein the silk elements are separated from each other by a distance between 1 µm and 100 µm.

11. A device as claimed in claim 1, wherein the packing density of the silk elements is in the range of from about 1 to about 30 per 10,000 µm$^2$.

12. A device as claimed in claim 1, wherein the tubular body has an external diameter of from about 1.0 to about 2.5 mm.

13. A device as claimed in claim 1, wherein the wall of the tubular body has a thickness of from about 250 µm to about 750 µm.

14. A device as claimed in claim 1, wherein the length of the device is from about 0.5 mm to about 20.0 mm.

15. A device as claimed in claim 1, wherein the silk elements have a diameter of from about 5 µm to about 50 µm.

16. A device as claimed in claim 1, wherein the silk elements comprise mulberry silkworm silk, non-mulberry silkworm silk, spider dragline silk, and filaments spun from recombinant silk protein or protein analogues.

17. A device as claimed in claim 16, wherein the silk elements are made from the silk derived from non-mulberry silkworms.

18. A device as claimed in claim 17, wherein the silk elements are in the form of sliver silk or reeled silk or twisted silk.

19. A device as claimed in claim 1, wherein the silk elements have a principal silk protein containing at least eight repeats of the triplet RGD.

20. A device as claimed in claim 19, wherein at least some of the repeats of the triplet RGD are located immediately adjacent to turns or predicted turns of a structure of the principal silk protein.

21. A device as claimed in claim 19, wherein the principal silk protein has sites from which one or more arginine groups of the principal protein has been blocked to tune cell adhesiveness.

22. A device as claimed in claim 21, wherein the blocking has been achieved by one or more of deamination, sulfation, amide formation and blocking with cyclohexanedione.

23. A device as claimed in claim 1, wherein the plurality of silk elements are set in a lumen matrix comprising a resorbable biocompatible polymer.

24. A device as claimed in claim 23, wherein the resorbable biocompatible polymer comprises a hydrogel.

25. A device as claimed in claim 24, wherein the hydrogel is hyaluronic acid or alginate, or casein.

26. A device as claimed in claim 1, wherein the lumen or the silk elements additionally comprises extracellular matrix.

27. A device as claimed in claim 26, wherein the extracellular matrix comprises fibronectin and/or laminin.

28. A device as claimed in claim 1, wherein the device additionally comprises one or more biologically active substances.

29. A device as claimed in claim 28, wherein the biologically active substances are selected from the group consisting of growth factors, cytokines, antibiotics, immunosuppressants, steroids, and non-steroidal anti-inflammatory drugs (NSAIDs).

30. A device as claimed in claim 1, wherein the device additionally comprises a population of cells.

31. A device as claimed in claim 30, wherein the cells are Schwann cells or olfactory ensheathing cells (OECs).

32. A method of manufacturing a medical device for regeneration of nerve cells comprising forming the tubular body and introducing the silk elements into the lumen of the tubular body so as to lie substantially parallel to the long axis of the lumen of the tubular body.

33. A method as claimed in claim 32, wherein formation of the tubular body comprises the steps of:
preparing a former on which the tubular body is formed;
laying down fibers on the former;
applying a matrix to the fibers to form a composite body; and
removing the former.

34. A method as claimed in claim 33, further comprising cross-linking the matrix.

35. A method as claimed in claim 32 further comprising introducing a lumen matrix component between the silk elements within the lumen of the tube.

36. A method for the regeneration of nerve cells comprising the implantation of a medical device according to claim 1.

37. A method for the treatment or repair of a spinal cord injury comprising the implantation of a device according to claim 1.

38. A method for the treatment or repair of a peripheral nerve injury comprising the implantation of a device according to claim 1.

39. A device as claimed in claim 1 for use in the regeneration of nerve cells.

40. A device as claimed in claim 1 for use in the regeneration of nerve cells in the spinal cord.

41. A device as claimed in claim 1 for use in the regeneration of nerve cells in a peripheral nerve.

* * * * *